(12) United States Patent
Vidlund et al.

(10) Patent No.: US 11,478,249 B2
(45) Date of Patent: Oct. 25, 2022

(54) OPHTHALMIC ARTERY THERAPY UNDER REVERSE FLOW

(71) Applicant: J.D. Franco & Co., LLC, Plano, TX (US)

(72) Inventors: Robert Vidlund, Forest Lake, MN (US); Michael Calhoun, Lighthouse Point, FL (US)

(73) Assignee: J.D. Franco & Co., LLC, Plano, TX (US)

(*) Notice: Subject to any disclaimer, the term of this patent is extended or adjusted under 35 U.S.C. 154(b) by 634 days.

(21) Appl. No.: 16/282,939

(22) Filed: Feb. 22, 2019

(65) Prior Publication Data

US 2019/0262000 A1 Aug. 29, 2019

Related U.S. Application Data

(60) Provisional application No. 62/634,325, filed on Feb. 23, 2018.

(51) Int. Cl.
| | |
|---|---|
| *A61B 17/12* | (2006.01) |
| *A61M 29/02* | (2006.01) |
| *A61F 2/01* | (2006.01) |
| *A61M 1/36* | (2006.01) |
| *A61B 17/22* | (2006.01) |

(52) U.S. Cl.
CPC .. *A61B 17/12109* (2013.01); *A61B 17/12036* (2013.01); *A61F 2/013* (2013.01); *A61M 29/02* (2013.01); *A61B 2017/22067* (2013.01); *A61M 1/3655* (2013.01); *A61M 2210/0612* (2013.01)

(58) Field of Classification Search
CPC ........ A61B 17/12109; A61B 17/12136; A61B 17/12036; A61F 2/013; A61M 2210/0612; A61M 29/02; A61M 1/3655
See application file for complete search history.

(56) References Cited

U.S. PATENT DOCUMENTS

| | | |
|---|---|---|
| 2,690,595 A | 10/1954 | Raiche |
| 3,367,101 A | 2/1968 | Garnet et al. |
| 3,435,826 A | 4/1969 | Fogarty |
| 4,403,612 A | 9/1983 | Fogarty |
| 4,445,897 A | 5/1984 | Ekbladh et al. |

(Continued)

FOREIGN PATENT DOCUMENTS

| | | |
|---|---|---|
| WO | WO 98/52639 A1 | 11/1998 |
| WO | WO 98/53761 A1 | 12/1998 |

(Continued)

OTHER PUBLICATIONS

Altinbas, N.K. et al, "Effect of Carotid Artery Stenting on Ophthalmic Artery Flow Patterns," Journal of Ultrasound Medicine, 2014; 33: pp. 629-638.

(Continued)

*Primary Examiner* — Sarah A Simpson
(74) *Attorney, Agent, or Firm* — Bookoff McAndrews, PLLC (57) ABSTRACT

A method may include positioning a first device within an internal carotid artery of a subject and impeding antegrade blood flow in the internal carotid artery. Additionally, the method may include delivering a pharmaceutical agent through an external carotid artery for passage into an ophthalmic artery of the subject.

20 Claims, 4 Drawing Sheets

(56) References Cited

U.S. PATENT DOCUMENTS

| | | |
|---|---|---|
| 4,926,858 A | 5/1990 | Gifford, III et al. |
| 5,026,384 A | 6/1991 | Farr et al. |
| 5,176,693 A | 1/1993 | Pannek, Jr. |
| 5,336,234 A | 8/1994 | Vigil et al. |
| 5,395,311 A | 3/1995 | Andrews |
| 5,419,761 A | 5/1995 | Narayanan et al. |
| 5,709,701 A | 1/1998 | Parodi |
| 5,820,595 A | 10/1998 | Parodi |
| 5,897,567 A | 4/1999 | Ressemann et al. |
| 5,972,019 A | 10/1999 | Engelson et al. |
| 6,146,370 A | 11/2000 | Barbut |
| 6,206,868 B1 | 3/2001 | Parodi |
| 6,302,908 B1 | 10/2001 | Parodi |
| 6,336,933 B1 | 1/2002 | Parodi |
| 6,344,054 B1 | 2/2002 | Parodi |
| 6,413,235 B1 | 7/2002 | Parodi |
| 6,423,032 B2 | 7/2002 | Parodi |
| 6,540,712 B1 | 4/2003 | Parodi et al. |
| 6,595,980 B1 | 7/2003 | Barbut |
| 6,623,471 B1 | 9/2003 | Barbut |
| 6,626,861 B1 | 9/2003 | Hart et al. |
| 6,641,573 B1 | 11/2003 | Parodi |
| 6,645,222 B1 | 11/2003 | Parodi et al. |
| 6,824,558 B2 | 11/2004 | Parodi |
| 6,827,726 B2 | 12/2004 | Parodi |
| 6,837,881 B1 | 1/2005 | Barbut |
| 6,855,162 B2 | 2/2005 | Parodi |
| 6,902,540 B2 | 6/2005 | Dorros et al. |
| 6,905,490 B2 | 6/2005 | Parodi |
| 6,908,474 B2 | 6/2005 | Hogendijk et al. |
| 6,929,634 B2 | 8/2005 | Dorros et al. |
| 6,936,053 B1 | 8/2005 | Weiss |
| 6,936,060 B2 | 8/2005 | Hogendijk et al. |
| 7,214,201 B2 | 5/2007 | Burmeister et al. |
| 7,235,095 B2 | 6/2007 | Haverkost et al. |
| 7,309,334 B2 | 12/2007 | Von Hoffmann |
| 7,604,612 B2 | 10/2009 | Ressemann et al. |
| 7,806,906 B2 | 10/2010 | Don Michael |
| 7,867,273 B2 | 1/2011 | Pappas et al. |
| 7,901,445 B2 | 3/2011 | Walker et al. |
| 7,927,347 B2 | 4/2011 | Hogendijk et al. |
| 8,157,760 B2 | 4/2012 | Carido et al. |
| 8,353,850 B2 | 1/2013 | Ressemann et al. |
| 8,414,516 B2 | 4/2013 | Chang |
| 8,545,432 B2 | 10/2013 | Renati et al. |
| 8,834,404 B2 | 9/2014 | Beaudin |
| 8,852,226 B2 | 10/2014 | Gilson et al. |
| 8,863,631 B1 | 10/2014 | Janardhan et al. |
| 9,078,682 B2 | 7/2015 | Lenker et al. |
| 9,241,699 B1 | 1/2016 | Kume et al. |
| 9,259,215 B2 | 2/2016 | Chou et al. |
| 9,265,512 B2 | 2/2016 | Garrison et al. |
| 9,987,164 B2 | 6/2018 | Calhoun |
| 2001/0001114 A1 | 5/2001 | Tsugita et al. |
| 2002/0087128 A1 | 7/2002 | Paques et al. |
| 2002/0143291 A1 | 10/2002 | Slater |
| 2002/0151922 A1 | 10/2002 | Hogendijk et al. |
| 2003/0023200 A1 | 1/2003 | Barbut et al. |
| 2003/0023227 A1 | 1/2003 | Zadno-Azizi et al. |
| 2003/0040694 A1* | 2/2003 | Dorros ............... A61B 17/22 604/8 |
| 2003/0199802 A1* | 10/2003 | Barbut ............... A61M 1/3613 604/4.01 |
| 2003/0199819 A1 | 10/2003 | Beck |
| 2003/0203958 A1 | 10/2003 | Kunz et al. |
| 2005/0149117 A1 | 7/2005 | Khosravi et al. |
| 2006/0136022 A1 | 6/2006 | Wong, Jr. et al. |
| 2006/0259132 A1 | 11/2006 | Schaffer et al. |
| 2007/0026035 A1 | 2/2007 | Burke et al. |
| 2008/0027519 A1 | 1/2008 | Guerrero |
| 2008/0243229 A1 | 10/2008 | Wallace et al. |
| 2009/0018455 A1 | 1/2009 | Chang |
| 2009/0024072 A1 | 1/2009 | Criado et al. |
| 2009/0030323 A1 | 1/2009 | Fawzi et al. |
| 2010/0125244 A1 | 5/2010 | McAndrew |
| 2011/0143993 A1 | 6/2011 | Langer et al. |
| 2011/0152683 A1 | 6/2011 | Gerrans et al. |
| 2011/0160762 A1 | 6/2011 | Hogendijk et al. |
| 2011/0319754 A1* | 12/2011 | Solar ............... A61M 1/3613 600/433 |
| 2012/0046679 A1 | 2/2012 | Patel et al. |
| 2012/0078287 A1 | 3/2012 | Barbut |
| 2012/0101510 A1 | 4/2012 | Lenker et al. |
| 2013/0035628 A1 | 2/2013 | Garrison et al. |
| 2013/0197621 A1 | 8/2013 | Ryan et al. |
| 2013/0281788 A1 | 10/2013 | Garrison |
| 2014/0154246 A1 | 6/2014 | Robinson et al. |
| 2015/0173782 A1* | 6/2015 | Garrison ........... A61M 25/0068 606/127 |
| 2015/0313607 A1 | 11/2015 | Zhadkevich |
| 2015/0366580 A1 | 12/2015 | Lenihan et al. |
| 2016/0166754 A1 | 6/2016 | Kassab et al. |

FOREIGN PATENT DOCUMENTS

| | | |
|---|---|---|
| WO | WO 00/54673 A1 | 9/2000 |
| WO | WO 03/018085 A2 | 3/2003 |
| WO | WO 2007/103464 A2 | 9/2007 |
| WO | WO 2014/022866 A1 | 2/2014 |
| WO | WO 2016/109586 A1 | 7/2016 |
| WO | WO 2017/156333 A1 | 9/2017 |
| WO | WO 2018/053121 A1 | 3/2018 |
| WO | WO 2018/106858 A1 | 6/2018 |

OTHER PUBLICATIONS

Ambarki, K. et al., "Blood Flow of Ophthalmic Artery in Healthy Individuals Determined by Phase-Contrast Magnetic Resonance Imaging," Investigative Ophthalmology & Visual Science, 2013; 54: pp. 2738-2745.

Hayreh, S.S., "The Ophthalmic Artery III. Branches," British Journal of Ophthalmology, 1962, 46, pp. 212-247.

Hwang, G. et al., "Reversal of Ischemic Retinopathy Following Balloon Angioplasty of a Stenotic Ophthalmic Artery." Journal of Neuro-Ophthalmology 30.3, 2010, pp. 228-230.

Kane, A.G. et al., "Reduced Caliber of the Internal Carotid Artery: A Normal Finding with Ipsilateral Absence or Hypoplasia of the A1 Segment," American Journal of Neuroradiology, 1996; 17: pp. 1295-1301.

Kawa, M.P. et al., "Complement System in Pathogenesis of AMD: Dual Player in Degeneration and Protection of Retinal Tissue," Hindawi Publishing Corporation, Journal of Immunology Research, vol. 2014, Article ID 483960, 12 pages.

Klein, R. et al., "Vasodilators, Blood Pressure-Lowering Medications, and Age-Related Macular Degeneration," American Academy of Ophthalmology, 2014, vol. 121, Issue 8, pp. 1604-1611.

Kooragayala, K. et al., "Quanitification of Oxygen Consumption in Retina Ex Vivo Demonstrates Limited Reserve Capacity of Photoreceptor Mitochondria," Investigative Ophthalmology & Visual Science, 2015; 56: pp. 8428-8436.

Krejza, J. et al., "Carotid Artery Diameter in Men and Women and the Relation to Body and Neck Size," Stroke, 2006; 3 pages.

Lanzino, G. et al., "Treatment of Carotid Artery Stenosis: Medical Therapy, Surgery, or Stenting?," Mayo Clinic Proceedings, Apr. 2009; 84(4), pp. 362-368.

Michalinos, A. et al., "Anatomy of the Ophthalmic Artery: A Review concerning Its Modern Surgical and Clinical Applications," Hindawi Publishing Corporation, Anatomy Research International, vol. 2015, Article ID 591961, 8 pages.

Paques, M. et al., "Superselective ophthalmic artery fibrinolytic therapy for the treatment of central retinal vein occlusion." British Journal of Ophthalmology, 2000, 84: 1387-1391.

Tan, P.L. et al., "AMD and the alternative complement pathway: genetics and functional implications," Human Genomics, 2016, 10:23, 13 pages.

Xu, H. et al., "Targeting the complement system for the management of retinal inflammatory and degenerative diseases," European Journal of Pharmacology, 2016, 787, pp. 94-104.

(56) References Cited

OTHER PUBLICATIONS

Yamane, T. et al., "The technique of ophthalmic arterial infusion therapy for patients with intraocular retinoblastoma," International Journal of Clinical Oncology, Apr. 2004; vol. 9, Issue 2, pp. 69-73.
Zeumer, H. et al., "Local intra-arterial fibrinolytic therapy in patients with stroke: urokinase versus recombinant tissue plagminogen activator (r-TPA)," Neuroradiology, 1993; 35: pp. 159-162.
Zipfel, P.F., et al., "The Role of Complement in AMD," Inflammation and Retinal Disease: Complement Biology and Pathology, Advances in Experimental Medicine and Biology, 2010, 703, pp. 9-24.
Examination Report No. 2 for AU Application No. 2013296195, dated Jun. 27, 2017 (6 pages).
Notice of Allowance for KR 20157005602, dated Sep. 25, 2017 (3 pages).
Loh, K. et al., "Prevention and management of vision loss relating to facial filler injections." Singapore Medical Journal, 2016; 57(8): 438-443.
International Search Report and Written Opinion for International Application No. PCT/US2017/051551, dated Dec. 15, 2017 (14 pages).
International Search Report and Written Opinion for International Application No. PCT/US2017/052901, dated Dec. 8, 2017 (9 pages).
International Search Report and Written Opinion for International Application No. PCT/US2018/031229, dated Jul. 27, 2018 (19 pages).
Bird, B. et al., "Anatomy, Head and Neck, Ophthalmic Arteries," NCBI Bookshelf, a service of the National Library of Medicine, National Institutes of Health, Oct. 27, 2018, 5 pages.
www.ncbi.nlh.nih.gov/books/NBK482317/?report=printable.
Hattenbach, L. et al., "Experimental Endoscopic Endovascular Cannulation: A Novel Approach to Thrombolysis in Retinal Vessel Occlusion," Investigative Ophthalmology & Visual Science, Jan. 2012, vol. 53, No. 1, pp. 42-46.
Khan, T.T. et al., "An Anatomical Analysis of the Supratrochlear Artery: Considerations in Facial Filler Injections and Preventing Vision Loss," Aesthetic Surgery Journal, 2017, vol. 37(2), pp. 203-208.
Schumacher, M. et al., "Intra-arterial fibrinolytic therapy in central retinal artery occlusion," Neurology (1993) 35: pp. 600-605.
Schwenn, O.K. et al., "Experimental Percutaneous Cannulation of the Supraorbital Arteries: Implication for Future Therapy," Investigative Ophthalmology & Visual Science, May 2005, vol. 46, No. 5, pp. 1557-1560.
Wang, R. et al., "Evaluation of Ophthalmic Artery Branch Retrograde Intervention in the Treatment of Central Retinal Artery Occlusion (CRAO)," Medical Science Monitor, 2017, 23: pp. 114-120.
Zhao, W. et al. "Three-Dimensional Computed Tomographic Study on the Periorbital Branches of the Ophthalmic Artery: Arterial Variations and Clinical Relevance," Aesthetic Surgery Journal, 2018, pp. 1-9.
International Search Report and Written Opinion for corresponding PCT/US2013/053670, dated Dec. 26, 2013 (16 pp.).
Hayreh et al., "Ocular Arterial Occlusive Disorders and Carotid Artery Disease," American Academy of Ophthalmology, 2017; vol. 1, No. 1: pp. 12-18.
Hayreh et al., "The Ophthalmic Artery," Brit. J. Ophthal., 1962; 46, 65: pp. 65-98.

* cited by examiner

OPHTHALMIC ARTERY THERAPY UNDER REVERSE FLOW

CROSS-REFERENCE TO RELATED APPLICATIONS

This patent application claims the benefit of priority under 35 U.S.C. § 119 to U.S. Provisional Patent Application No. 62/634,325, filed Feb. 23, 2018, which is herein incorporated by reference in its entirety.

TECHNICAL FIELD

Various aspects of the present disclosure relate generally to medical systems, devices, and related methods. More specifically, the present disclosure relates to medical systems and/or devices for delivering pharmaceutical therapy under reverse blood flow.

BACKGROUND

Vasculature of a subject (also referred to as patient) may occasionally become stenosed, occluded, partially occluded, blocked, narrowed, or otherwise compromised such that transfer of blood through the vasculature is impeded, lessened, and/or prevented. That is, the blood carrying capacity of such a compromised vessel is reduced or otherwise insufficient. The vasculature may become occluded, stenosed, or at least partially blocked due to the deposit of plaque, emboli, or other such material on the walls of the vasculature. To avoid serious and/or permanent injury, one or more medical procedures or interventions may be performed. Such procedures may include, for example, angioplasty, atherectomy, stenting, or the like in which a constricted, narrowed, occluded, or otherwise partially blocked region of the vasculature is opened, widened, or unblocked so as to allow or maintain blood flow therethrough. Additionally, such procedures may involve delivery of a pharmaceutical agent to treat, reduce the size of, break apart or fragment a clot or other such tissue or blockage within the constricted, narrowed, occluded, or otherwise partially blocked region of the vasculature so as to provide a therapeutic benefit to the patient. Often such procedures further dilate the artery and loosen and/or fragment plaque, emboli, or other such material. The fragmented plaque, emboli, or other material may travel downstream with a flow of blood passing through the vasculature and potentially result in a stroke or other embolic event.

The systems, devices, and methods of the current disclosure may rectify some of the deficiencies described above or address other aspects of the prior art.

SUMMARY

Examples of the present disclosure relate to, among other things, medical devices and procedures. Each of the examples disclosed herein may include one or more of the features described in connection with any of the other disclosed examples.

In one example, a method may include positioning a first device within an internal carotid artery of a subject and impeding antegrade blood flow in the internal carotid artery. Additionally, the method may include delivering a pharmaceutical agent through an external carotid artery for passage into an ophthalmic artery of the subject.

In another example, a method may include impeding antegrade blood flow in an internal carotid artery of a subject via a first device and positioning a distal end of a second device distally of a junction between an external carotid artery and a common carotid artery. The method may also include delivering a pharmaceutical agent via the second device through the external carotid artery for passage into an ophthalmic artery of the subject.

In a further example, a method may include impeding antegrade blood flow in an internal carotid artery of a subject via a first device and delivering a pharmaceutical agent through an external carotid artery for passage into an ophthalmic artery of the subject. Additionally, the method may include treating a blockage, a stenosis, a lesion, plaque, or other physiology in the ophthalmic artery or a junction between the ophthalmic artery and the internal carotid artery.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not necessarily include only those elements but, may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical systems, devices, and methods for treating internal areas of a patient's body by establishing reverse blood flow in the OA, and delivering a pharmaceutical agent to the OA via the induced reverse blood flow pathway.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to a medical professional using the medical device or insertion device. In contrast, "distal"

refers to a position relatively further away from the medical professional using the medical device or insertion device, or closer to the interior of the body.

The terms "downstream" or "antegrade" and "upstream" or "retrograde," when used herein in relation to the subject's vasculature, refer respectively, to the direction of blood flow and the direction opposite that of blood flow, respectively. In the arterial system, "downstream" or "antegrade" refers to the direction further from the heart, while "upstream" or "retrograde" refers to the direction closer to the heart.

"Reverse flow," as used herein, is the flow of blood opposite to the direction of blood flow under normal blood flow conditions. In this disclosure, "reverse flow" and "retrograde flow" are used synonymously. Reverse flow may be achieved by creating a pressure gradient, so blood flow is reversed and directed, for example, from the treatment site into a lumen of a medical device to be rerouted to another location.

Figure 1:
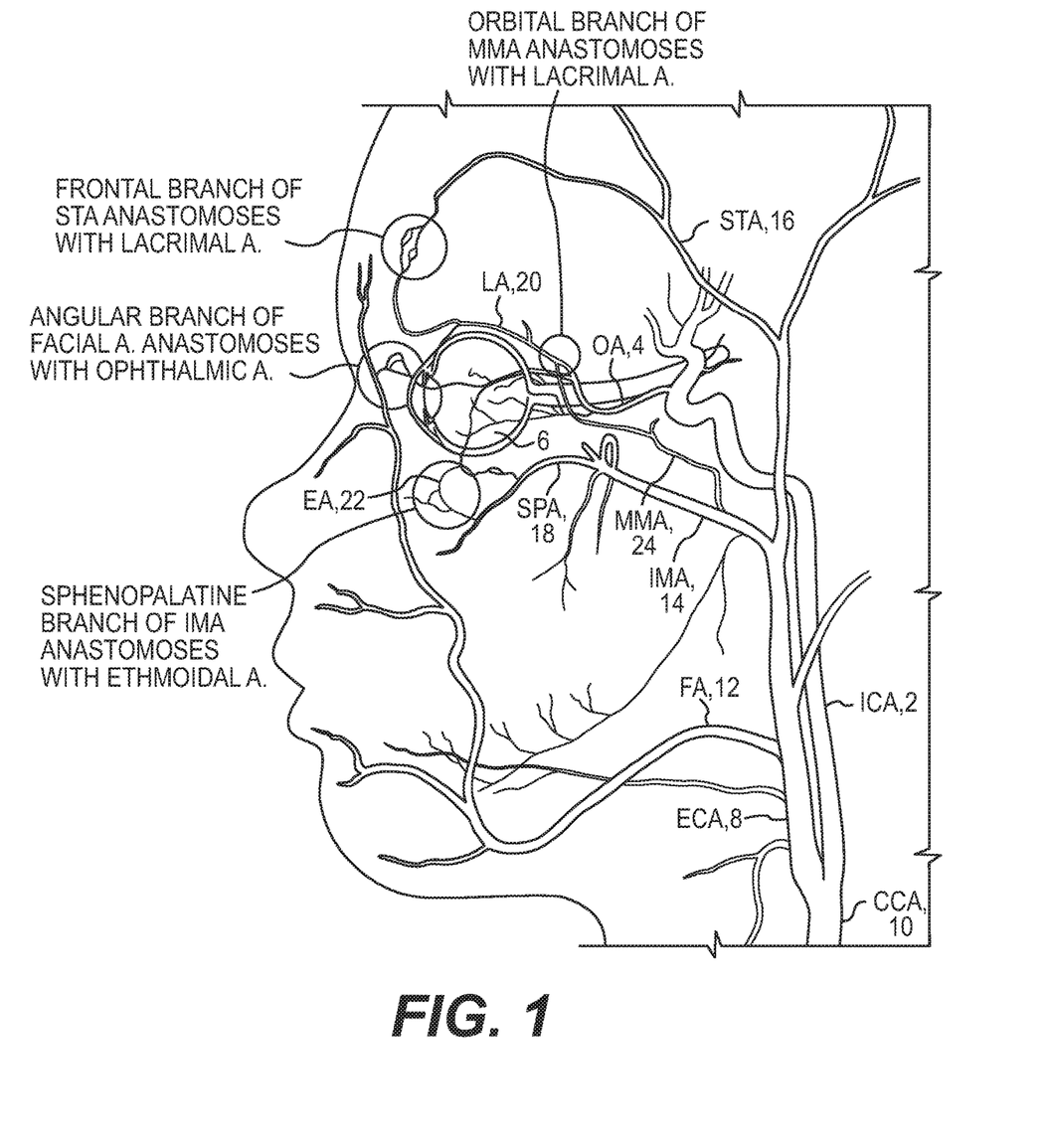
FIG. 1 illustrates vasculature of and relating to an ophthalmic artery (OA) of a subject.

FIG. 1 illustrates various vasculature structures of a subject. For example, blood may flow from the heart (not shown) through the internal carotid artery (ICA) 2 to the ophthalmic artery (OA) 4 to an eye 6 of the subject. Additionally, the external carotid artery (ECA) 8 may supply a flow of blood to the face and neck of a subject. Both the ICA 2 and ECA 8 branch off from the common carotid artery (CCA) 10 of the subject. The ECA 8, in turn, branches into the facial artery (FA) 12, the internal maxillary artery (IMA) 14, and the supra trochlear artery (STA) 16. The IMA 14 then branches into the sphenopalatine artery (SPA) 18, and the middle meningeal artery (MMA) 24. The OA 4 includes a number of branches such as the lacrimal artery (LA) 20 and the ethmoidal artery (EA) 22. ICA 2 and ECA 8 have several anastomoses (e.g., connections or junctures) which permit the exchange of blood therebetween. Specifically, the anastomoses that relate to OA 4 include: (1) anastomosis between SPA 18 and EA 22 (indicated at arrow 4 of FIG. 2); (2) anastomosis between MMA 24 and LA 20 (indicated at arrow 2 of FIG. 2); (3) anastomosis between STA 16 and LA 20 (indicated at arrow 1 of FIG. 2); and (4) anastomosis between FA 12 and OA 4 (indicated at arrow 3 of FIG. 2).

Figure 2:
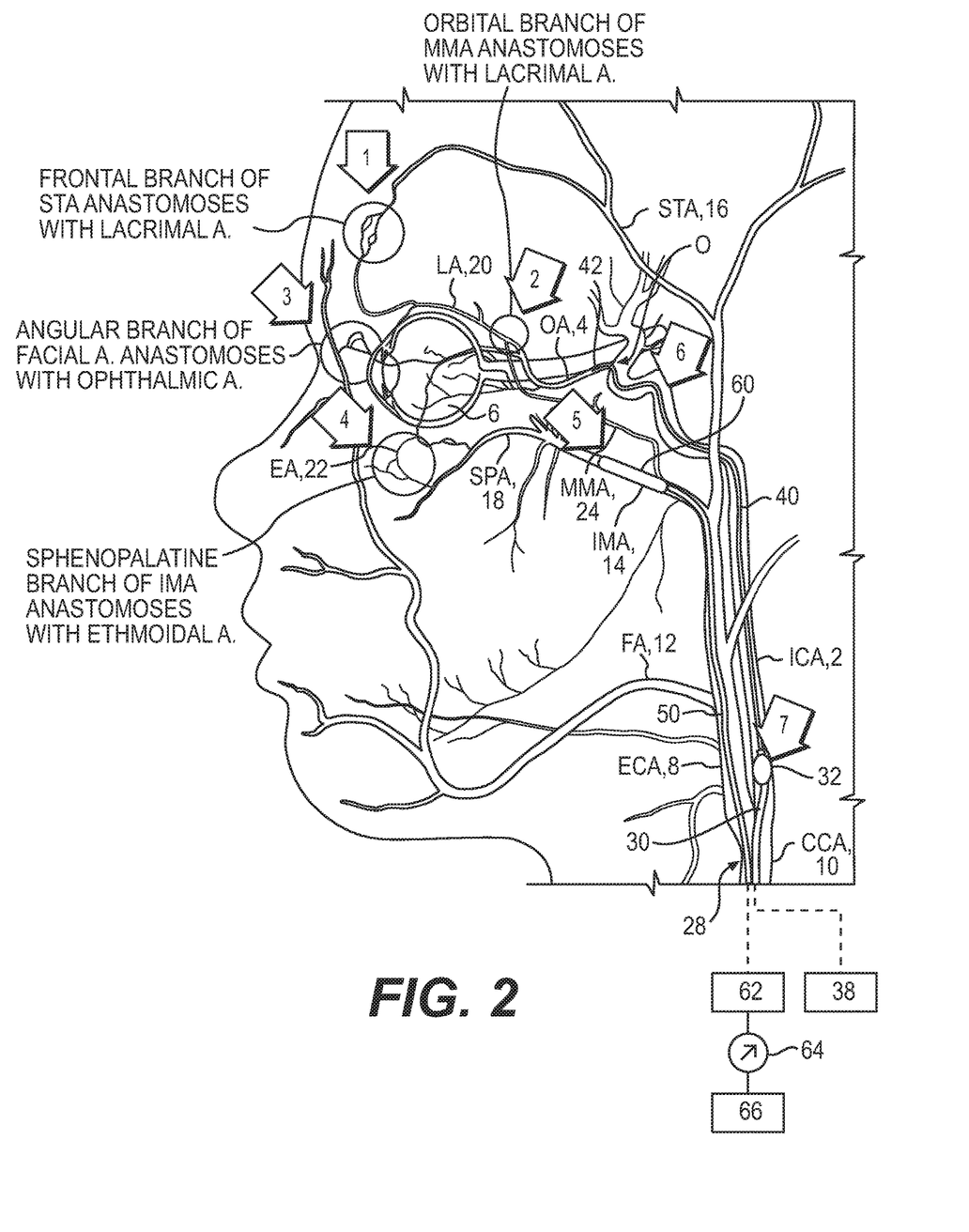
FIG. 2 illustrates an exemplary system for delivering a pharmaceutical agent via reverse flow delivery to the OA.

FIG. 2 illustrates an exemplary system 28 for establishing reverse flow in OA 4 and delivering one or more pharmaceutical agents thereto. As shown in FIG. 2, such a system may include a sheath 30 and an inflatable balloon 32. Balloon 32 may be mounted on or positioned about an external surface of sheath 30. In some arrangements, balloon 32 may be formed as a cuff encircling a portion (e.g., a distal end portion) of sheath 30. Balloon 32 may be a compliant balloon and constructed of any appropriate materials (e.g., urethane polymer or thermoplastic rubber elastomer). Balloon 32 may have any appropriate shape and size. For example, upon expansion of balloon 32, a cross-sectional dimension (e.g., diameter) of balloon 32 may be sized so as to contact a wall of ICA 2. That is, a cross-sectional dimension (e.g., diameter) of balloon 32 in an expanded state may average about 4.62 mm, or a sufficient diameter so as to occlude the ICA 2 and prevent the passage of blood.

Sheath 30 (e.g., a catheter) may include a plurality of lumens. At least one of such lumens may be a balloon inflation lumen having a first end fluidly coupled with a source of inflation fluid 38 (e.g., a gas such as air, or a liquid such as water or saline) and a second end fluidly coupled to an interior of balloon 32 via a side port/valve (not shown), such that upon delivery of fluid from source 38 to balloon 32, balloon 32 may expand from a first, uninflated configuration (not shown) to an expanded configuration as shown in FIG. 2. Additionally, the first lumen may be coupled to a source (not shown) of negative pressure (e.g., vacuum) such that upon actuation of the negative pressure source, balloon 32 may be deflated. Alternatively, source 38 may be a reversible source and may be toggled (e.g., manually or automatically) between a positive pressure state for balloon 32 inflation/expansion and a negative pressure state for balloon 32 evacuation.

A second lumen of sheath 30 may extend between a proximal end and a distal end of sheath 30, e.g., distal to balloon 32. The second lumen may be a guide lumen such that sheath 30 and balloon 32 may be delivered over a guidewire or the like via the second lumen. Such a second lumen may be configured for "rapid exchange" (RE) delivery or "over-the-wire" (OTW) delivery.

A sheath 40 may be delivered through the second lumen of sheath 30 to a location distal of sheath 30. For example, as shown in FIG. 2, sheath 40 may be navigated through ICA 2 and into OA 4. In some arrangements, sheath 40 may be inserted through an ostium O between the ICA 2 and OA 4 and into a short limb 15 of OA 4. In other arrangements, sheath 40 may extend only into the ostium O between ICA 2 and OA 4. In still further arrangements, sheath 40 may remain within ICA 2 throughout use. In any such arrangement, sheath 40 may be arranged to deliver one or more interventional devices to a location within OA 4. For example, such an interventional device 42 may include one or more of an artherectomy device, an angioplasty device (e.g., an angioplasty balloon), and a distal protection device (e.g., basket or expandable filter device), as will be described in further detail below. Interventional device 42 may be delivered into OA 4 to perform any appropriate medical intervention, as will be described in further detail below.

An additional catheter 50 may be advanced into ECA 8. Notably, a distal end 52 of catheter 50 may be positioned at any location within ECA 8 (or an associated branch of ECA 8) distal of the junction between ICA 2, ECA 8, and CCA 10. In the arrangement shown in FIG. 2, for example, distal end 52 of catheter 50 is delivered distally of a junction between ECA 8 with FA 12, and into IMA 14. Optionally, however, distal end 52 of catheter 50 may be positioned within ECA 8, FA 12, MMA 24, or STA 16, as deemed desirable or necessary by a medical professional.

Once so positioned, a pharmaceutical agent 60 may be delivered from a source 62 fluidly coupled with catheter 50. The pharmaceutical agent 60 may include, but is not limited to, any one or more of vasodilators (e.g., adenosine, PDE5 inhibitors, nitric oxide donors, and epinephrine), thrombolytics (e.g., urokinase, streptokinase, anistreplase, and recombinant tissue plasminogen activators), antioxidants (e.g., uric acid, glutathione, melatonin, dismutase, catalase, peroxiredoxins, and thioredoxin), anti-coagulants (e.g., heparin, coumadin, and synthetic penta saccharides), ACE inhibitors (e.g., perindopril, captopril, benazepril, and zofenopril), antihistamines (e.g., diphenhydramine, loratadine, fexofenadine and hydroxyzine), beta blockers (e.g., propranolol, carvedilol, and oxprenolol), calcium channel blockers (e.g., aranidipine, lacidipine, nifedipine, and nitrendipine), NSAIDS (e.g., ibuprofen, and naproxen), and/or corticosteroids (e.g., cortisol, corticosterone, cortisone, and aldosterone). These may also include families of diuretics, angiotensin II receptor antagonists, adrenergic receptor antagonist, renin inhibitors, aldosterone receptor antagonists, alpha-2 adrenergic receptor agonists, endothelin receptor blockers or any pharmaceutical or combination of pharmaceutics that provide a benefit to the vasculature.

Pharmaceutical agent 60 may be delivered via a lumen of catheter 50 from a pharmaceutical source 62. Optionally, perfusion of pharmaceutical agent 60 may be pressurized via a pressurizer 66 (e.g., syringe, power injector, pump, etc.). Pressurizer 66 may be either an automatic or manually operated pressurizer. For example, an automatic pressurizer may include a motor (not shown) to deliver a constant source of pressure to the pharmaceutical agent 60. Alternatively, a manual pressurizer (e.g., syringe) may be employed to provide a medical professional with selective control of the pressure of perfusion of pharmaceutical agent 60. Optionally, pressurizer 66 may be controlled via a regulator 64 to ensure appropriate pressurization of pharmaceutical agent 60. Pressurization of pharmaceutical agent 60 may be desired depending on one or more of a tortuosity of the anatomical location of distal end 52 of the catheter 50, a cross-sectional dimension (e.g., diameter) of the lumen of catheter 50, a cross-sectional dimension of a target anatomical location for perfusion of pharmaceutical agent, and/or a composition (e.g., viscosity, etc.) of pharmaceutical agent 60. While references throughout the present disclosure relate to delivery of pharmaceutical agent 60, the disclosure is not so limited. Rather, any appropriate diagnostic and/or therapeutic fluid/agent may be delivered as described herein via catheter 50. Examples of such diagnostic and/or therapeutic fluid/agents may include: ionic contrast media (e.g., barium sulfate, propyliodone, iodoxamic acid, metrizamide and diatrizoic acid), nonionic contrast media (e.g., barium sulfate), paramagnetic contrast media (e.g., gadobenic acid, gadolinium, and mangafodipir), super magnetic contrast media (e.g., ferumoxsil, ferristene, and iron oxide) and contrast agents (e.g., dyes, and radiologic tracers).

In use, a medical professional may access ICA 2 via any appropriate manner (e.g., an arterial cut down, etc.). Additionally, the medical professional may position a guidewire within the vasculature of a subject, extending an end of the guidewire into ICA 2 to a position distal of a junction between CCA 10 and ECA 8. Once so positioned, sheath 30 may be advanced over the guidewire into position within ICA 2. Radiopaque or other markers may be positioned on one or more portions of sheath 30 so as to assist in longitudinal and rotational positioning of sheath 30 and balloon 32 via suitable imaging or other viewing techniques. Once sheath 30 is positioned, the guidewire may be removed from the lumen of sheath 30. Alternatively, the guidewire may remain within the lumen during a remainder of the procedure.

Next, balloon 32 may be expanded, as shown at arrow 7 of FIG. 2. That is, source 38, coupled to the first lumen of sheath 30 may be actuated so as to inflate balloon 32. Upon expansion of balloon 32, balloon 32 may contact a wall of ICA 2. Due to expansion of balloon 32, antegrade blood flow through ICA 2 may be prevented or blocked. However, as balloon 32 is positioned distal of the junction between CCA 10 and ECA 8, antegrade blood flow between CCA 10 and ECA 8 is maintained. That is, inflation of balloon 32 prevents or blocks only antegrade blood flow of ICA 2. Such a continuation of antegrade flow between CCA 10 and ECA 8 serves to supply various OA 4 to ECA 8 anastomoses including: (1) anastomosis between SPA 18 and EA 22; (2) anastomosis between MMA 24 and LA 20; (3) anastomosis between STA 16 and LA 20; and (4) anastomosis between FA 12 and OA 4 (FIG. 1). The antegrade flow of blood from CCA 10 and ECA 8 is maintained in order to ensure that an adequate supply of blood is available via the common anastomoses such that continuous retrograde movement of blood is ensured from OA 4 to ICA 2. While all of these anastomoses may not be present in every patient, enough of them are typically present to offer the potential pathway for feeding OA 4 and ICA 2 with a blood supply to ensure continuous retrograde flow during reverse flow procedures. As such, any plaque, emboli, or other material dislodged and/or fragmented may be prevented from flowing from OA 4 or ICA 2 toward the eye 6, thereby preventing an embolic event (e.g., blindness, stroke, etc.). Additionally, a proximal end of sheath 30 may be coupled to a filter and a return line (not shown) to return the filtered retrograde blood flow into a venous return site (e.g., into the internal jugular vein (IJV) of the subject) via any appropriate manner. Any plaque, emboli, or other material within the flow of retrograde blood is trapped in the filter and removed from the vascular system with the removal of the filter from the vascular system.

Additionally, catheter 50 may be advanced into the arterial system and arranged so as to perfuse a pharmaceutical agent 60 into ECA 8, or one or more branches thereof (indicated at arrow 5 of FIG. 2). For example, distal end 52 of catheter 50 may be positioned within IMA 14 and fluidly coupled with source 62 (and optionally, regulator 64 and/or pressurizer 66) to perfuse the pharmaceutical agent 60 into the arterial system. Due to the anastomoses between SPA 18 and EA 22, and the anastomosis between MMA 24 and LA 20, the pharmaceutical agent 60 is delivered to OA 4 so as to treat (e.g., break apart) a clot, stenosis, or other obstructive or partially obstructive material positioned within the OA 4 or ostium O between OA 4 and ICA 2. As such material is broken apart or fragmented, such material may be carried with the flow of retrograde blood through ICA 2, into sheath 30, through a filter to collect and remove any fragmented material or particulate and returned into the venous system via the venous return site (e.g., into the internal jugular vein (IJV) of the subject) via a shunt or like.

Optionally, interventional device 42 may be advanced through sheath 40 and into OA 4 (indicated at arrow 6 of FIG. 2). For example, interventional device 42 may include any one or more of a guidewire, a balloon (e.g., a drug eluting (DE) balloon or a non-drug-eluting (POBA) balloon), an atherectomy device, a distal protection device (e.g., fragment capture portion such as a basket), and/or a stent, etc. Such an interventional device 42 may be advanced into OA 4 for one or more additional procedures, including those described in detail in International Patent Application Publication No. WO 2014/022866, which is incorporated by reference herein in its entirety.

Figure 3A:
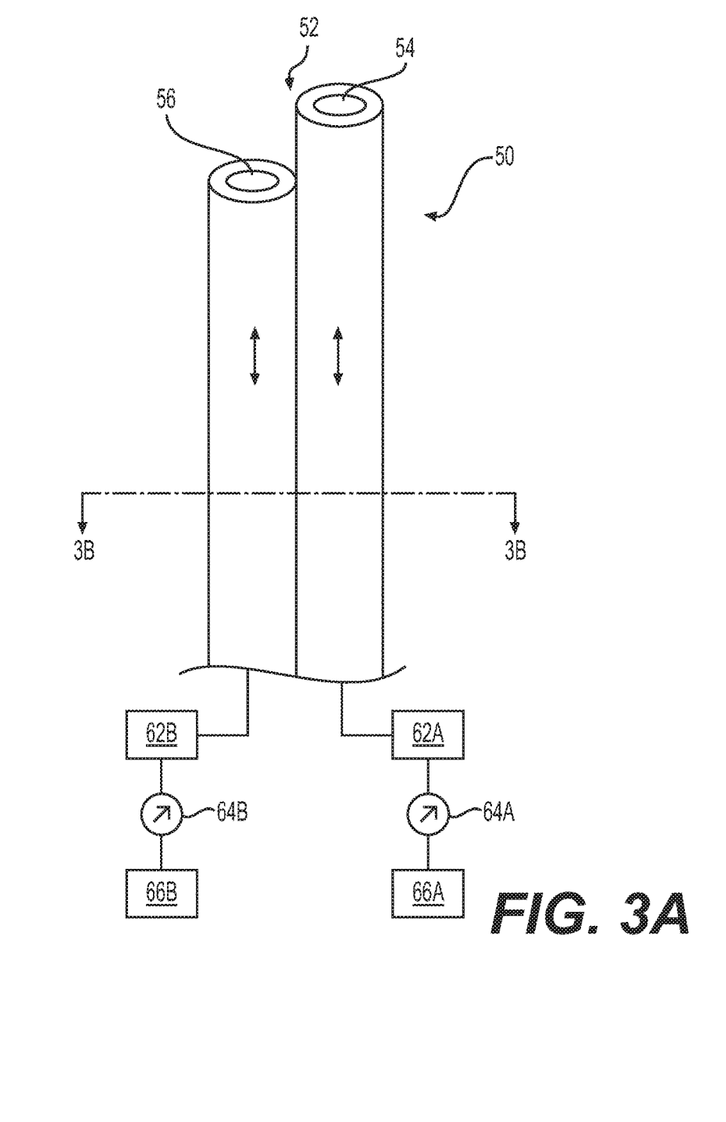
FIG. 3A illustrates an exemplary catheter for delivery of a pharmaceutical agent.

In some arrangements, catheter 50 may be a multi-lumen catheter. In such an arrangement, a first pharmaceutical agent may be perfused into the arterial system of a patient via a first lumen of catheter 50, while a second pharmaceutical agent may be perfused into the arterial system of a patient via a second lumen of catheter 50. For example, as shown in FIG. 3A, catheter 50 may include first lumen 54 and second lumen 56. As shown, each of first lumen 54 and second lumen 56 may be movable relative to one another and independently of the other. In such a way, a first pharmaceutical agent may be delivered to a first location of the arterial system of a subject, while a second pharmaceutical agent may be delivered to a second location of the arterial system of a subject. For example, in some arrangements, first lumen 54 may be arranged such that a distal end thereof is positioned in MMA 24, while second lumen 56 may be arranged such that a distal end thereof is positioned within IMA 14. In another arrangement, one of first lumen 54 and second lumen 56 may be advanced into FA 12, while the other of first lumen 54 and second lumen 56 is positioned within STA 16. It is understood that such arrangements are merely exemplary and in other arrangements, one of first lumen 54 and second lumen 56 may be positioned in any one of ECA 8, FA 12, IMA 14, MMA 24, and STA 16, while the other of first lumen 54 and second lumen 56 may be positioned in another one of ECA 8, FA 12, IMA 14, MMA 24, and STA 16. To position each of first lumen 54 and second lumen 56 as desired, a guide wire may first be deployed into the desired location, and the first lumen 54 or second lumen 56 may be delivered along the guidewire. In some arrangements, the first pharmaceutical agent and the second pharmaceutical agent may have a common chemical composition. In other arrangements, the first pharmaceutical agent 60 (delivered via first lumen 54) and the second pharmaceutical agent 60 (delivered via second lumen 56) may have differing chemical compositions. For example, the first pharmaceutical agent 60 may be urokinase, while the second pharmaceutical agent 60 may be streptokinase.

Figure 3B:
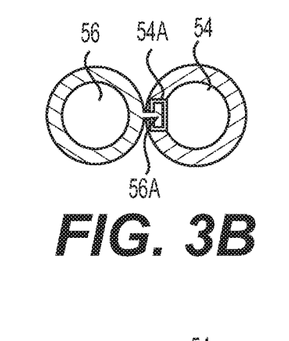
FIG. 3B illustrates a cross-sectional view of the catheter of FIG. 3A, taken along line 3B-3B.
Figure 3C:
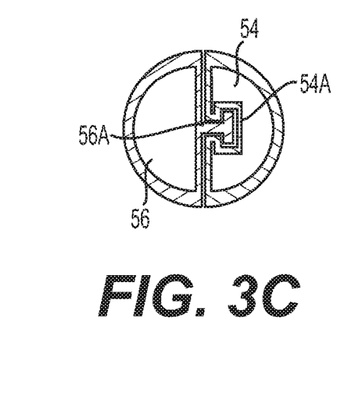
FIG. 3C illustrates a cross-sectional view of an additional embodiment of an exemplary catheter for delivery of a pharmaceutical agent.

As shown, first lumen 54 is coupled to second lumen 56. To facilitate relative movement between first lumen 54 and second lumen 56 of catheter 50, a wall defining first lumen 54 may include an opening, track, or groove 54A, while a wall defining second lumen 56 may include a correspondingly shaped or configured protrusion 56A for being mated to or received within groove 54A, as shown in FIG. 3B. Upon receipt of protrusion 56A within groove 54A, first lumen 54 may slide or translate relative to second lumen 56, or vice versa. In further arrangements, a wall defining second lumen 56 may include an opening, track, or groove, while a wall defining first lumen 54 may include a correspondingly shaped or configured protrusion. Additionally, while each of first lumen 54 and second lumen 56 are illustrated as including a circular cross-sectional shape, the disclosure is not so limited. For example, as shown in FIG. 3C, a cross-sectional shape of each of first lumen 54 and second lumen 56 may be generally D-shaped. In other arrangements, first lumen 54 may have a cross-sectional shape or size different than second lumen 56.

Figure 4:
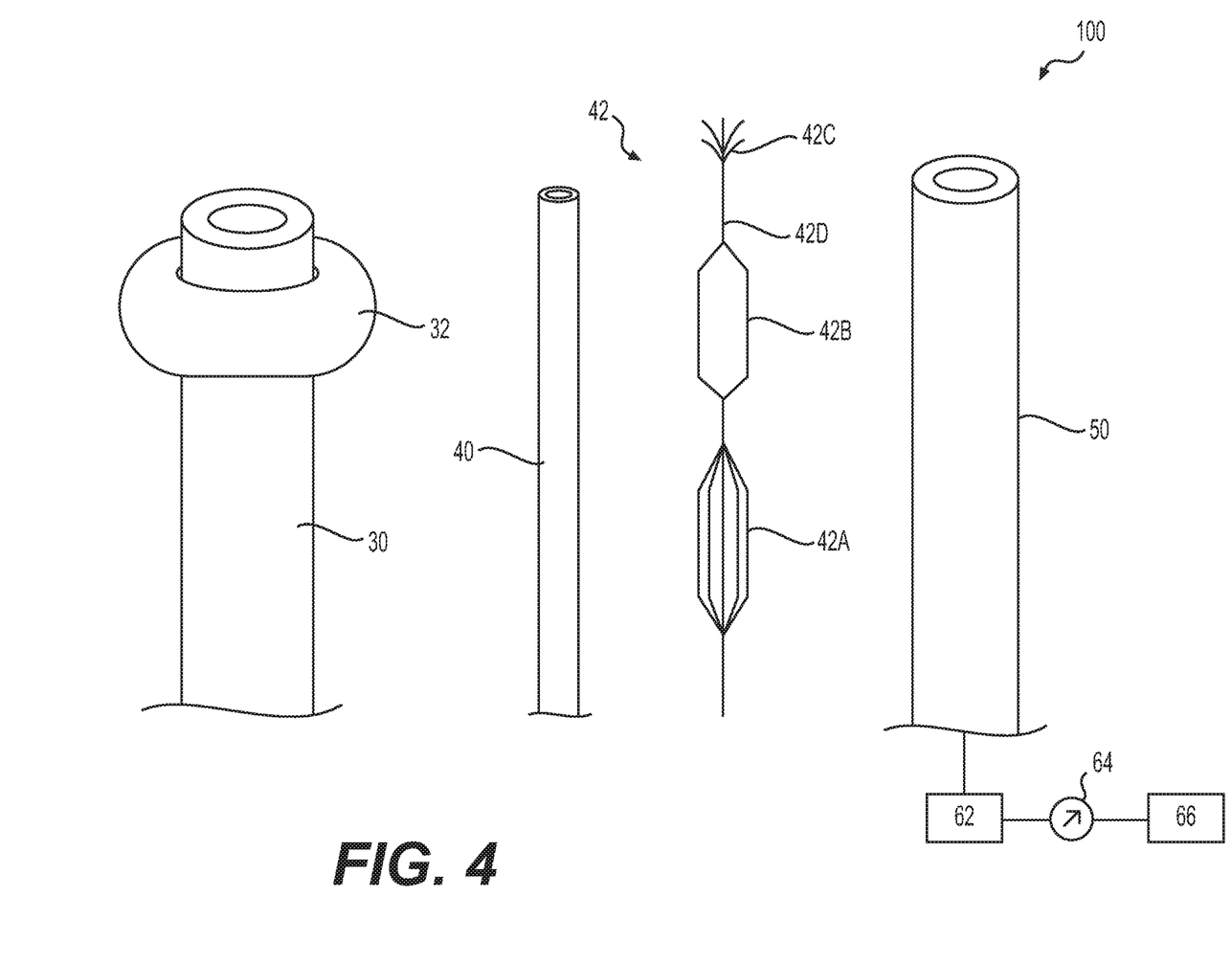
FIG. 4 illustrates an exemplary kit according to aspects of the present disclosure.

In some aspects, an exemplary kit 100, as shown in FIG. 4, includes a sheath 30 including a balloon 32. While only a single sheath 30 is illustrated, kit 100 may include a variety of sheaths 30 of varying dimensions (e.g., cross-sectional dimension (or diameter) or length). Additionally, kit 100 may include sheath 40 and an exemplary interventional device 42. Interventional device 42 may include an atherectomy portion 42A, an angioplasty portion 42B, and a distal protection (e.g., capture) portion 42C positioned along a common core wire 42D. Optionally, core wire 42D may be tubular and may be arranged for connection to a source of aspiration, if needed or desired. Each of atherectomy portion 42A, angioplasty portion 42B, and distal protection portion 42C may be sized and shaped for delivery into OA 4. Additionally, in some arrangements, one or more of atherectomy portion 42A, angioplasty portion 42B, and a distal protection portion 42C may not be connected to core wire 42D, but rather may be coupled to a separate guidewire so as to be axially translatable to another of atherectomy portion 42A, angioplasty portion 42B, and distal protection portion 42C. Again, it is understood that while only a single interventional device 42 is illustrated, kit 100 may include a variety of interventional devices. Additionally, kit 100 may include catheter 50 for delivery of one or more pharmaceutical agents. As discussed above, catheter 50 may also be coupled to a source 62 of pharmaceutical agent 60, a pressurizer (e.g., pump) 66, and a regulator 64 for controlled perfusion of pharmaceutical agent 60. While kit 100 is illustrated as including a single catheter 50 having only one lumen, the disclosure is not so limited. Rather, kit 100 may include a multi-lumen catheter as discussed above in connection with FIGS. 3A-3C. Additionally, kit 100 may include exemplary directions for use (DFU), not shown, to guide a medical professional during the use of kit 100.

While principles of the present disclosure are described herein with reference to illustrative examples for particular applications, it should be understood that the disclosure is not limited thereto. For example, in any of the above noted arrangements, rather than returning induced retrograde blood flow through a filter and into a venous return site, the blood may be removed via a source of negative pressure (e.g., suction from a syringe) and discarded. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A method, comprising:
   positioning a first device within an internal carotid artery of a subject;
   impeding antegrade blood flow in the internal carotid artery so as to induce retrograde blood flow in an ophthalmic artery of the subject; and
   delivering a pharmaceutical agent to an artery of the subject other than the internal carotid artery in an antegrade direction for passage via an anastomotic pathway into the ophthalmic artery of the subject in a retrograde direction, wherein the artery other than the internal carotid artery of the subject is downstream of an external carotid artery of the subject.

2. The method of claim 1, wherein the impeding antegrade blood flow includes expanding an occlusion device within the internal carotid artery.

3. The method of claim 2, wherein the expanding the occlusion device within the internal carotid artery includes expanding the occlusion device at a location within the internal carotid artery closer to a junction with a common carotid artery than a junction with the ophthalmic artery.

4. The method of claim 1, wherein the delivering the pharmaceutical agent includes delivering the pharmaceutical agent under pressure.

5. The method of claim 4, further comprising controlling a pressure of the pharmaceutical agent via a regulator.

6. The method of claim 1, further comprising delivering a second device through a lumen of the first device such that a distal end of the second device is positioned in the ophthalmic artery or a junction between the ophthalmic artery and the internal carotid artery.

7. The method of claim 6, further comprising treating a blockage, a stenosis, a lesion, plaque, or other physiology in the ophthalmic artery or the junction between the ophthalmic artery and the internal carotid artery.

8. The method of claim 1, further comprising, prior to the delivering the pharmaceutical agent, positioning a delivery device such that a distal end of the delivery device is located distally of a junction between an external carotid artery and a common carotid artery of the subject.

9. The method of claim 8, wherein the positioning the delivery device includes positioning the distal end of the delivery device within the other than the internal carotid artery of the subject.

10. The method of claim 8, wherein the positioning the delivery device includes positioning the distal end of the delivery device within an internal maxillary artery, a facial artery, a middle meningeal artery, or a supra trochlear artery.

11. The method of claim 1, wherein the pharmaceutical agent includes a vasodilator, a thrombolytic, an antioxidant, an anti-coagulant, an ACE inhibitor, an antihistamine, a beta blocker, a calcium channel blocker, an NSAID, a corticosteroid, or combinations thereof.

12. A method, comprising:
impeding antegrade blood flow in an internal carotid artery of a subject via a first device, so as to induce retrograde blood flow in an ophthalmic artery of the subject;
positioning a distal end of a second device distally of a junction between an external carotid artery and a common carotid artery of the subject; and
delivering a pharmaceutical agent via the distal end of the second device, to an artery of the subject other than the internal carotid artery in an antegrade direction for passage via an anastomotic pathway into the ophthalmic artery of the subject such that the pharmaceutical agent travels in a retrograde direction, wherein the artery other than the internal carotid artery of the subject is downstream of the external carotid artery of the subject.

13. The method of claim 12, wherein the positioning the distal end of the second device includes positioning the distal end of the second device within the artery other than the internal carotid artery of the subject.

14. The method of claim 12, wherein the positioning the distal end of the second device includes positioning the distal end of the second device within an internal maxillary artery, a facial artery, a middle meningeal artery, or a supra trochlear artery.

15. The method of claim 12, wherein the delivering the pharmaceutical agent includes delivering the pharmaceutical agent under pressure.

16. The method of claim 12, wherein the pharmaceutical agent includes a vasodilator, a thrombolytic, an antioxidant, an anti-coagulant, an ACE inhibitor, an antihistamine, a beta blocker, a calcium channel blocker, an NSAID, a corticosteroid, or combinations thereof.

17. The method of claim 12, further including treating a blockage, a stenosis, a lesion, plaque, or other physiology in the ophthalmic artery or a junction between the ophthalmic artery and the internal carotid artery.

18. A method, comprising:
impeding antegrade blood flow in an internal carotid artery of a subject via a first device, so as to induce retrograde blood flow into an ophthalmic artery of the subject;
delivering a pharmaceutical agent at an arterial site other than the internal carotid artery in an antegrade direction for passage via an anastomotic pathway into the ophthalmic artery of the subject such that the pharmaceutical agent travels in a retrograde direction, wherein the artery other than the internal carotid artery of the subject is downstream of an external carotid artery of the subject; and
treating a blockage, a stenosis, a lesion, plaque, or other physiology in the ophthalmic artery or a junction between the ophthalmic artery and the internal carotid artery.

19. The method of claim 18, further comprising, prior to the delivering the pharmaceutical agent, positioning a delivery device such that a distal end of the delivery device is located distally of a junction between the external carotid artery and a common carotid artery.

20. The method of claim 19, wherein the positioning the delivery device includes positioning the distal end of the delivery device within an internal maxillary artery, a facial artery, a middle meningeal artery, or a supra trochlear artery.

* * * * *

UNITED STATES PATENT AND TRADEMARK OFFICE
CERTIFICATE OF CORRECTION

PATENT NO. : 11,478,249 B2
APPLICATION NO. : 16/282939
DATED : October 25, 2022
INVENTOR(S) : Robert Vidlund and Michael Calhoun It is certified that error appears in the above-identified patent and that said Letters Patent is hereby corrected as shown below:

In the Claims

In Claim 9, Column 8, Line 62, "other" should read as --artery other--.

Signed and Sealed this
Twentieth Day of December, 2022

Katherine Kelly Vidal
Director of the United States Patent and Trademark Office